United States Patent [19]

Gaddum

[11] 4,064,745

[45] Dec. 27, 1977

[54] METHOD OF PROVIDING REPRESENTATION OF AGING OF MATERIAL

[76] Inventor: Friedbert Gaddum, Schulstrasse 6, 3031 Ahlden, Aller, Germany

[21] Appl. No.: 688,420

[22] Filed: May 20, 1976

[30] Foreign Application Priority Data

May 21, 1975 Germany .............................. 2522362

[51] Int. Cl.$^2$ ............................................. G01N 3/32
[52] U.S. Cl. ....................................................... 73/91
[58] Field of Search .................. 73/91, 100, 95, 88 R, 73/89, 86

[56] References Cited

U.S. PATENT DOCUMENTS 2,659,232  11/1953  Lubahn .................................... 73/89

OTHER PUBLICATIONS

Holt, et al., "A Method of Measuring Relaxation Stress for Aluminum Alloys," J. of Basic Engineering, Sept., 70, (pp. 655–661).

*Primary Examiner*—Anthony V. Ciarlante
*Attorney, Agent, or Firm*—Ralf H. Siegemund

[57] ABSTRACT

Specimens are subjected to dislocation (tensile extension, compression, torsion) in discontinuous steps in which load and no-load conditions alter during work cycles, interspaced by recovery periods. The length of each work cycle is determined to be much shorter than required for a dynamic equilibrium state. The recovery periods may be terminated in closed loop operation. The reaction force peaks at the beginning and the end of each work cycle, the force differential in beginning and end of each load cycle phase, and the force level resulting from a low level displacement bias during recovery are parameters indicating aging and other properties. Artificial aging may continue throughout.

6 Claims, 5 Drawing Figures

METHOD OF PROVIDING REPRESENTATION OF AGING OF MATERIAL

BACKGROUND OF THE INVENTION

The present invention relates to the determination of the effect aging has on mechanical properties and conditions of objects, e.g. specimens of plastic, synthetic, and other materials.

Methods are known according to which a specimen is alternatingly subjected to a load and relieved from that load. The load condition is carried out by deforming the object (specimen) in a particular manner. For example, the specimen is extended for a particular distance (stress load), or the specimen is subjected to torsion by twisting it by a particular angle, or the specimen is compressed, or subjected to shear force etc., and the reaction force in the specimen is measured. Generally speaking, one will test and work the material in a manner that may represent the dominating wear and load conditions of the specific subsequent use. On the other hand, the material may include or be subjected to forced aging and one wants to know the progress of that process.

Many plastic materials, polymers, elastomers, etc., can be tested in that manner and the differences in (elastic) reaction forces is indicative of aging. In between two tests, the specimen may be subjected to artificial aging processes such as heating, cooling, subjecting the specimens to gases, radiation, liquids, etc.

Particularly after such aging the measurments proceeded in a manner that the specimen is, e.g. alternatingly extended and relieved from the extension until the peak values of the reaction forces during a period of extension (loading) remained constant from each load-no-load cycle to the next one. In other words, one used an equilibrium condition as indication of the specific elastic state which, in turn, is to be indicative of aging. That equilibrium was, of course, dynamically obtained through the sequence of load-no-load cycles. Unfortunately, these equilibrium conditions do not occur rapidly but often after long periods of time up to an hour or even longer, and the material has to be worked through all this time by subjecting it to the sequence of load-no-load cycles. Aside from the operational (and economic) effort exerted therewith, long periods of working the specimens needed to attain the state of constant reaction force maxima from each load cycle phase to the next one, is a period in which the internal state of the specimen may change due to physical relaxation and/or chemical decomposing etc. Thus, the measurements purporting to represent aging may not be true on that account. The measurement is a composite of the effect of the discontinuous stress-relaxation working method and of other, parallel running, internal process. For this reason the equilibrium state may actually never be reached. This is particularly so if the specimen are subjected to aging fluids which remain in contact with the specimen during measurement; the aging process continues.

The German printed patent application P 24 47 624.2 discloses such a discontinuous stress-relaxation measurement and proposes to correct the specimen extension, e.g. by clamping the specimen anew after each load phase. This way, the actual extension exerted is the same from cycle to cycle, and one does not have to wait until a dynamic equilibrium with constant force peaks has been established. Thus, continuing aging and other internal processes will not falsify the measurement. However, the correcting operation is very cumbersome and expensive. One has to either clamp the specimen to the test equipment anew for each new load phase, or, as an alternative, one has to measure the needed length extension and provide the correction on that basis.

Another aspect is to be seen in the fact that frequently the first extension produces a much longer reaction than subsequent ones which is due to an ordering process in the material. This ordering process is actually superimposed and tends to introduce errors in the recognition of aging.

DESCRIPTION OF THE INVENTION

It is an object of the present invention to simplify the method of discontinuous stress-relaxation working of a specimen for purposes of determining aging.

It is a particular object of the present invention to eliminate the effect of internal ordering processes from the measurement of aging.

It is another object of the present invention to render the determination of age-dependent properties independent from equilibrium conditions in a discontinuous stress-relaxation process.

In accordance with the preferred embodiment, it is suggested to subject a specimen under investigation to an alternating sequence of work and recovery cycles, wherein each work cycle is comprised of a sequence of load no-load conditions on the specimen but each work cycle is relatively short so that reaction forces still change from each load phase to the next one, and each recovery period (with or without load on the specimen) is sufficient for obtaining internal recovery of the specimen. The reaction forces in the specimen are determined particularly during each work cycle but the determination may possibly continue throughout. The detected reaction force values serve as raw data for the generation of information indicative of aging.

Each work cycle is much shorter than the usual period covered by such alternating load- no-load cycles if one would wait until the reaction force maxima have leveled off during sequential load cycle phases. In other words, each work cycle lasts for a period of, say, less than 20 percent of the period it would take an uninterrupted sequence of load-no-load cycles to work the material into the above defined state of equilibrium, wherein the reaction force peaks of sequential load phases are in about the same level.

The new method is particulary suitable if the specimen include components with strong plastic (lasting) deformation. The plot of reaction force vs. time, particularly during any work cycle, yields considerable information, and the relation of any specific parameter to the analogous parameter obtained during a subsequent work cycle yields the information on aging.

Specifically and for a fixed duration of each work cycle, the maximum reaction force amplitude of the last load phase of each work cycle is a comparative indicator of the aging process. Another indication is the relaxation force differential during the last load phase. The first peak force amplitude at the beginning of each work cycle and the development in sequential work cycles, is an indication for the internal ordering process as the result of stretching.

It should be noted that recovery is a relative term and 70 to 80% of complete recovery may well be sufficient. The recovery period is usually a complex parameter and varies greatly. Therefor, it is suggested to use a low level bias during the recovery period and to determine when a constant reaction force has been established in the specimen serving as an indication that recovery has been completed. This permits alternation between work and recovery cycles in closed loop control. The length of the recovery period established in that manner is another indication of the aging process. The bias reaction force itself is another parameter of interest because the bias proper is produced by a specific (small) length extension of the sample or specimen; the resulting reaction force is another age indication.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2, is plotted against time and for different materials in representation of different aging processes as detectable with the inventive method and equipment.

Proceeding now to the detailed description of the drawings, FIG. 3 shows a device and equipment which includes two sample or specimen holders 1 and 2 in which a specimen 3 is held, e.g. by means of clamping. Specimen and holders are situated in a reaction vessel which can be heated up to a predetermined temperature. Moreover, the vessel has an inlet and an outlet so that a fluid may pass through such as a liquid or a gas, e.g. nitrogen or oxygen, or oil or any other aging fluid.

Figure 1:
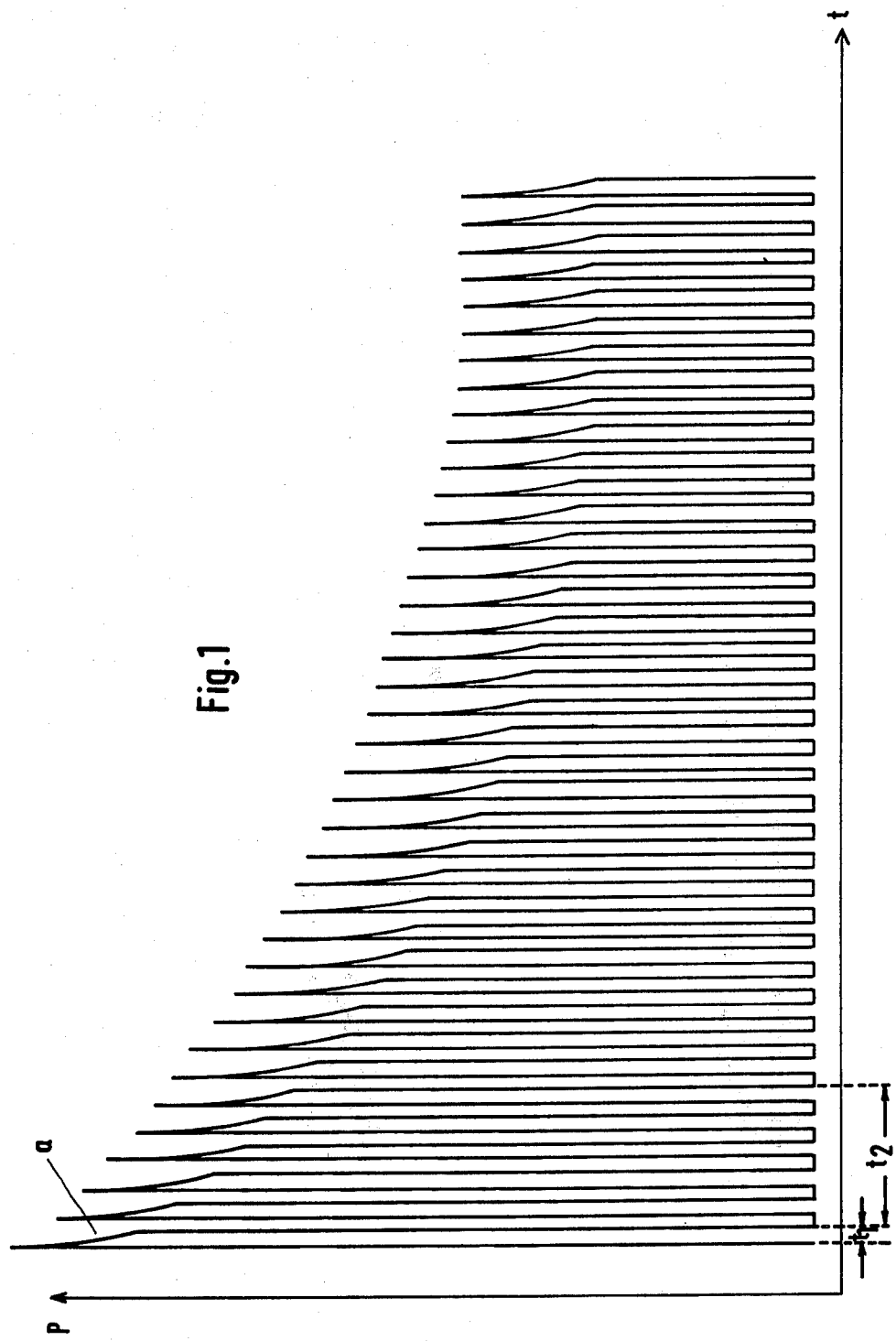
FIG. 1 is a plot of reaction force vs. time resulting from a discontinuous stress-relaxation process and demonstrating the problem of the prior art method in relation to one aspect of the inventive method.

Details of this vessel and reactor are not of interest per se. However, it is a specific advantage of the inventive method that the aging process, if so desired, can be continued or, at least, it may be stopped but without requiring the specimen to be removed from the aging equipment.

The lower specimen holder 2 is connected to a lift producing device 5, for example, a lifting magnet. The stroke of the holder 2 may be limited so that for each energizing pulse of the (negative) lift producing magnet, holder 2 is lowered corresponding to a particular length extension. It is important that the device 5 produces definite and, possibly, constant length extensions in the clamped and held specimen 3. Device 5 can return holder 2 to a lesser extension as will be explained below.

Block 6 denotes a control circuit for operating lifting device 5, specifically for obtaining a pulsating or oscillating stress load on the specimen 3 followed by relief from load. In other words, circuit 6 operates device 5 for up and down strokes and thereby produces alternating stress load-no-load cycles. Specifically, the device 5 is altered between stress load producing lowering and pauses, or periods of load relief. Thus, specimen 3 is discontinuously deformed by operation of the alternating lift strokes of device 5.

In lieu of clamping for obtaining tension and relief, one could provide for a compression device which cycles the specimen alternatingly through compression and no-compression cycles. Still alternatively, one could use means for generating a pulsating bending and/or torsion load, or one could provide plates with sandwiched specimens for obtaining a pulsating shear force load. One could also use a test worm which rotates in a cylinder to measure relaxation of highly viscous material. Generally speaking, the equipment provides for pulsating application of a mechanical load that produces a reaction force in the specimen and each such load pulse is followed by a period of relief from that load.

The upper clamp 1 is basically stationary but connected to a force meter or transducer 7 (in the case of torsionally loading the specimens one will need a torque meter etc.). The electrical signal produced by instrument 7 represents the force acting on specimen 3. The signal of transducer 7 is fed to the head 10 of a plotter 8, for plotting force vs. time on a strip chart 9. Plotters with movable heads etc. are known per se.

FIG. 1 is an example of a plot or curve plotted on a strip chart 9. The curve is force P (as measured) plotted against time $t$, resulting from strip chart advance. The "teeth" of this comb-like plot are reaction force value and as a whole, they represent the alternation between load and no-load conditions on the specimen. It is of great importance that the entire graph depicted in FIG. 1 extends over the entire period deemed necessary in the past for practicing prior art discontinuous stress-relaxation measurement. The load-no-load cyclic operation had to be continued until the force peaks produced during each load cycle phase remain at the same level from load cycle to load cycle and as shown in the right hand portion of the plot. As per the invention, each work cycle is limited to a much shorter period $t_2$ at the end of which the cyclic exertion of tensile stress is terminated! At this point, the peak reaction per load cycle is still declining from load cycle to the last load cycle.

The periods of loading and no-load conditions, i.e. the periods of exerting stress and relief are venienctly equal and denoted by $t_1$. They could be different but that was found unnecessary and similarity facilitates control. However, each work cycle has the same length $t_2$ so that the number of load cycles per work cycle is the same. Moreover, it is of particular interest that the external load conditions are constant during each load and stress producing cycle phase. That is to say, the specimen is subjected a particular displacement of the lower clamp 2 which remains constant during such a load phase. This way, it is possible to observe the relaxation of the material as it is being subjected to stress. As can be seen specifically from curve portions $a$, the reaction force detected and measured by transducer 7 is reduced already during the periods of enforced extension or elongation of the specimen. This reduction is the result of internal relaxation of the specimen. The reduction in force has a significant value for materials which are highly plastically deformable.

The known method of discontinously measuring relaxation caused force maxima to be measured during each loading step and one waited thereafter until the maxima leveled off to a constant value. As already mentioned, this is depicted in the right hand portion of FIG. 1. The known methods required this constancy and artificial aging could begin only thereafter, using that leveled-off maximum as a reference. In cases, this period may be up to an hour or even longer. Moreover, it was observed that, if aging continues, a constant level for the maximum was never really attained!

Figure 2:
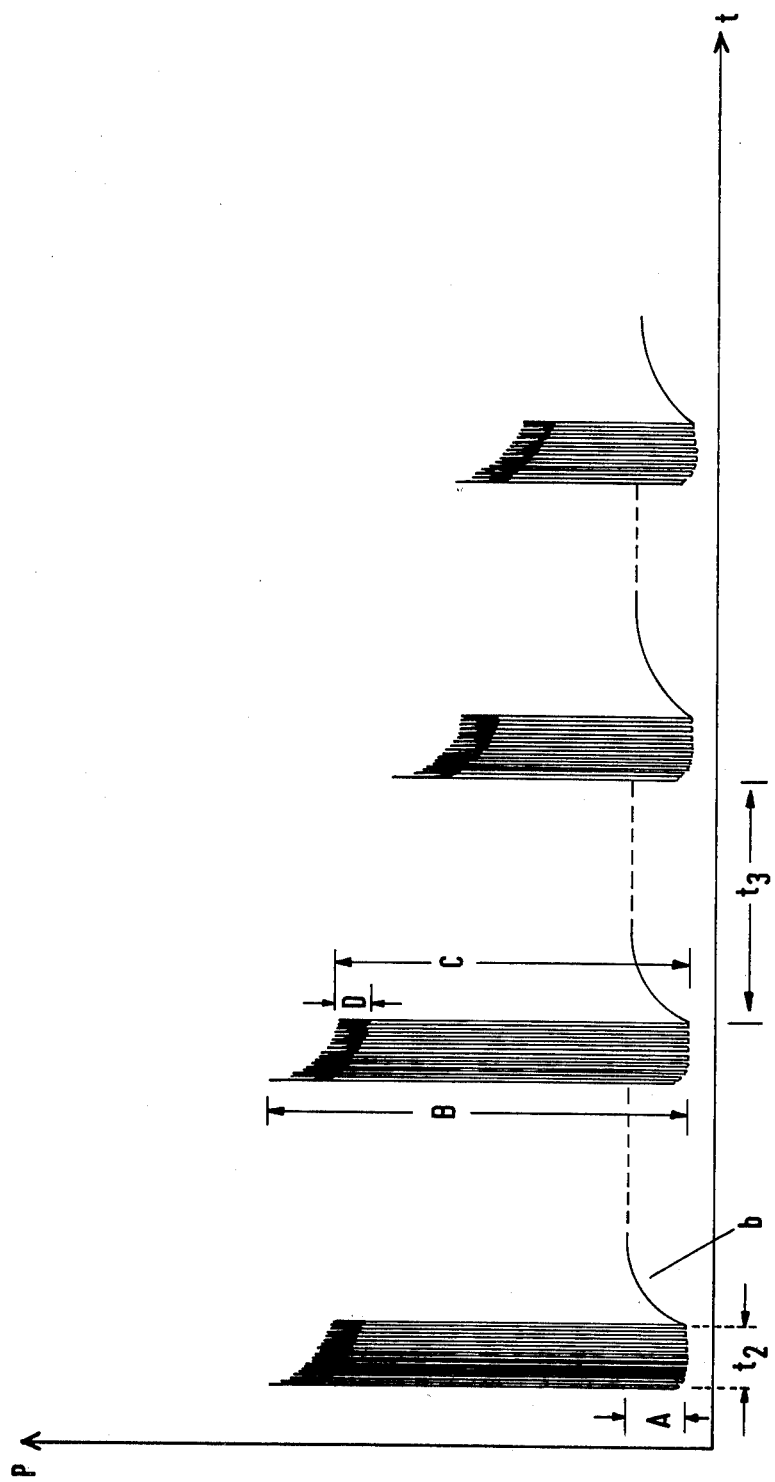
FIG. 2 is a similar type plot but on a smaller scale and as directly resulting from practicing the invention.

The inventive method avoids extension of the work period to last until the onset of a constant level for the maxima, because it was recognized that one does not have to wait until the maxima have a constant level for each load pulse in order to determine particulars of aging. It was found that the alternative of load application and relief can be halted already, e.g. at time $t_2$, which is about one to three minutes after a work cycle has begun. This way one obtains blocks or groups of readings as shown in FIG. 2. Active aging may continue through and the progress (if any) of the aging process can be determined by comparing the data and signal blocks with each other. There is one such signal or information block per work cycle period $t_2$.

The period $t_3$ in between two work cycles must be sufficient so that the specimen can recover at least to a substantial degree. The recovery period is not necessarily known, particularly because it may change on account of the aging process. Of course, one could select the period $t_3$ to be of sufficient length so that the specimen has recovered with certainty. However, a preferred mode of operation is the following.

One should hold the specimen in the recovery position so that during its recovery a particular small bias extension is exerted on the specimen. Such bias may also be advisable for the determination of the force zero point. In any event, following a period ($t_2$) of alternating load-no-load cycles, the length extension (position of clamp 2) is set to a non-zero value, so that the reaction force has contours as per curve b up to the value A.

As the reaction force reaches a constant value, the specimen has recovered. The force A is indicated by transducer 7, and can be used to start a new work cycle as will be described more fully below. Suffice it to say presently that such a fixed bias provides direct indication as to when the specimen has recovered, and a read-out by the plotter establishes directly such an indication and reading.

The information obtained by the inventive method can be used as follows. By way of example, the first two data blocks or groups of force excursions in FIG. 2 are similar in contour, amplitude, etc., which means that the specimen did not age in between the two work cycles. The third plotted signal group is smaller and the fourth one is still smaller which means that in between the second and third work cycles and the third and fourth work cycles the specimen did (or was) aged in the sense of a loss of strength and increased ductility. If successive blocks have larger amplitudes, this would indicate embrittlement of the specimen!

The type of aging is not so much derivable from the peak value B or reaction at the onset of each run and work cycle, because reaction to the first loading is to a significant extent determined by an internal ordering process. Decisive for the type of aging undergone by the specimen during two work cycles is the relation between the last peak C of each block or run, i.e. of the peak excursion during the last load cycle phase of any work cycle!

The quantity D is another indication of aging as it indicates directly relaxation during a stress load period, and the development of D during a work cycle as well as from work cycle to work cycle is another aging indicator. Spedifically, D is the difference in reaction force at the beginning and the end of each load and stress exerting cycle phase. This differential D represents the plastic portion of the specimen. Also, the force A resulting from a particular displacement and position bias of the specimen and the slope contour of curve b are all indicative of aging. Of course, the contour and slope of curve portion b is not only dependent upon ductility or embrittlement, but additionally upon the recovery as such.

It should be realized that these particular values, A, B, C, and D, do not only yield information to the intervening aging process, but they represent the elastic and viscous properties of the specimen as such. These values can be used to calculate the complex dynamic module of elasticity or a similar quantity. In addition, these values, A, B, C, D as extractable and derivable from the plotted signal block resutling from each work cycle, can be quantitatively referenced to each other and from block to block, i.e. work cycle to work cycle.

Figure 5:
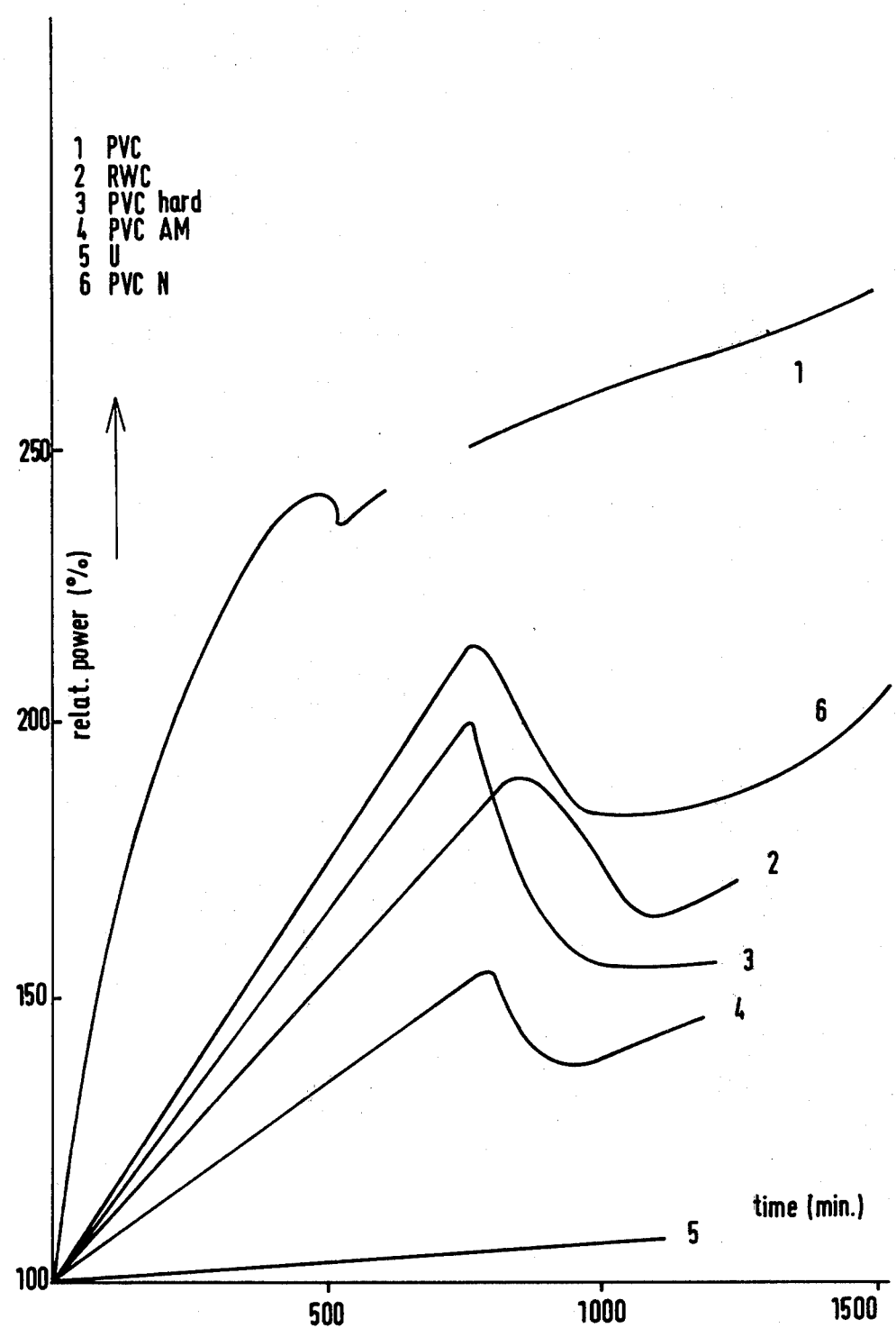
FIG. 5 is a graph in which a specific parameter extractable from the information gained as per

FIG. 5 shows the relative change of values C from block to block (on a percentage basis) and for different materials as specimen. The specimen differed in their content of age-proofing additives, and they were subjected to oil. It can readily be seen that all specimens became more brittle, the C-values increased from work cycle to work cycle. Specimen No. 1 aged very strongly, while specimen No. 5 was apparently quite age-proof, its brittleness increased very little and it aged very little accordingly.

Figure 3:
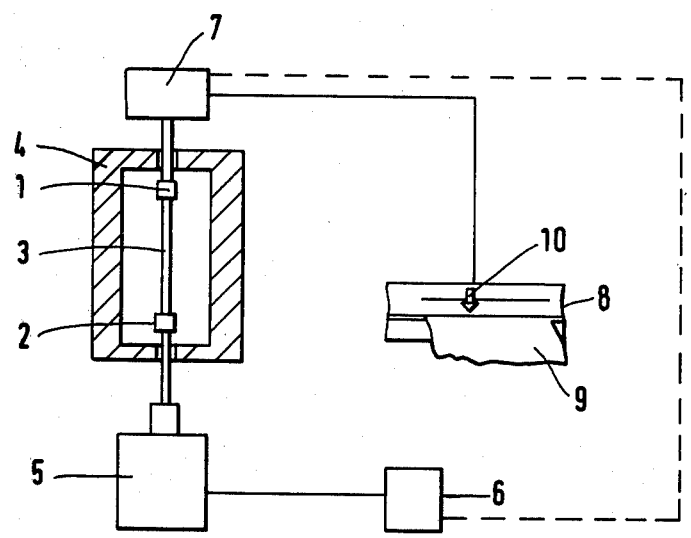
FIG. 3 is a schematic representation and block diagram for equipment used for practicing the invention, the plots as per FIGS. 1 and 2 have been generated by this type of apparatus.
Figure 4:
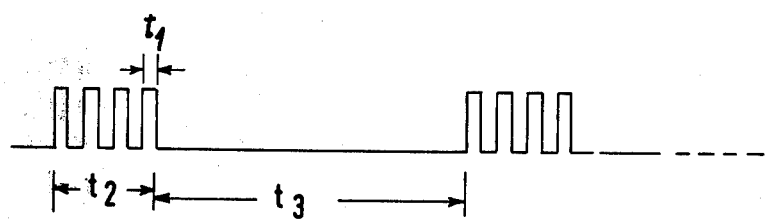
FIG. 4 is an operational pulse diagram plotted against time and representing the control of the equipment shown in FIG. 3.

Returning for the moment to FIG. 3, it is advisable to construct control 6 for fully automatic operation and to alternate its operation between relatively short ($t_2$) work cycles and longer pauses and recovery periods $t_3$. During each work cycle control 6 operates the lifting device 5 for alternating between lowering strokes and upward, load relief strokes. One does not need supervision of the process, provided, of course, the periods are adequately known in advance. FIG. 4 shows a diagram of activation pulses for the magnet in device 5 as provided by control circuit 6. Thus, control 6 produces bursts of pulses for a duration $t_2$ of each burst and a longer pause between two bursts. Each work cycle is defined by constantly spaced activation pulses of similar duration and height to produce particular length extensions. It should be noted, however, that the constant length extension is not necessarily the result of a constant energization pulse, but by mechanical set stops which limit the down displacement of the magnetic plunger in device 5 as moving the clamp 2. On the basis of FIG. 4, one can also see that the "zero" level in this graph may not necessarily represent zero extension or displacment during the period $t_3$, but a slight energizatio level is provided to obtain the bias extension of the specimen during two successive work cycles. The no-load periods during each work cycle should result in zero extension of the specimen.

The parameter D (difference of beginning and end values of force during a load phase) is quite important and must be discernible, which can be taken care of by a sufficient resolution in the horizontal: the strip chart must not move too slowly during a work cycle. However, in the alternative, one can make use of the fact that a fast lateral displacement of the plotter head 10 at the beginning and in the end of each load phase results in a rather thinly drawn plotting line because the head moves fast across the strip chart and a constant (in time) flow of ink will indeed result in a rather thin and unpronounced line. This, in turn, means that these lines can be placed very closely together. On the other hand, the plotting speed for portion D is slower than the very steep leading and trailing flanks of each load pulse. Thus, any portion D will be plotted more heavily and will be quite pronounced. This renders the value D and its development during a work cycle readily visible.

As a general rule, the periods $t_2$ and $t_3$ are not constant and should be adjustable. As per the principle of the invention, $t_2$ should be adjusted to be considerably shorter than the leveling off period as defined above. However, a particualr period $t_2$ may well accommodate a large variety of situations. More likely is a variation in $t_3$, as the desired and/or actually produced aging in between two runs and work cycles may vary. As far as the control circuit 6 is concerned, the energizing pulses may be produced by a low frequency oscillator with square wave output, and the period $t_2$ may be metered by an adjustable time relay which enables the output of the low frequency oscillator to provide (perferably via amplifiers or relays) the energizing pulses for the magnet or solenoid in device 5. The time relay is triggered at the end of each period $t_3$ which may be determined by another time relay metering the pause or recovery period. However, the device may operate in a closed loop. The dashed line in FIG. 3 represents that loop.

As soon as transducer 7 furnishes for a certain period of time the force value A as a steady signal, the next work cycle may begin. Thus, $t_3$ will not be a constant system period but is terminated whenever transducer 7 has sensed force level A for a certain period of time. Thus, circuit 6 may include an amplitude monitor as to the output of transducer 7 or it may include a differentiating circuit in that it periodically samples the output of transducer 7 and if two or several sequential values differ by less than a minimum, and if the same condition persists for a certain period of time (time relay) then the time relay metering the next work cycle is triggered. It should be noted that this way the recovery period $t_3$ between any two sequential work cycles becomes another parameter which is extractable from the device, because it represents the speed of recovery between two work cycles which may vary with age or otherwise.

It can readily be seen that the principles of the invention can be practiced with a variety of equipment. FIG. 3 illustrates just a simple device by means of which tension load can be exerted upon a specimen and under controlled conditions. The control may be provided electronically, electrically or electromechanically, e.g. by means of cams which control alternating lowering and relief strokes. In cases one may exert sinusoidal extensions upon the sample.

Another modification is to hold the specimen under load during the pauses. The recovery being of a different nature in such a case. Other forms of loading were already mentioned, e.g. compression, torsion, shear, bending, etc., but it must still include several load-no-load cycles in order to permit production of meaningful information. One of the parameters to be selected is the period of the work cycle $t_2$. As a general rule, $t_2$ is much smaller than the recovery period.

The invention is not limited to the embodiments described above but all changes amd modifications thereof not constituting departures from the spirit and scope of the invention are intended to be included.

I claim:

1. Method of determining and measuring aging and-/or age-dependent properties of a specimen comprising the following steps:

first, subjecting the specimen to alternating mechanical load-no-load conditions for a period during which the maximum reaction force effective during sequential load phases still declines;

second interrupting the first mentioned step for a period longer than a period needed for about 70% to 80% recovery of the specimen, the recovery being or would be completed when, following a load change, the reaction force has again reached a constant level;

repeating the first and second steps in cyclic fashion; and measuring the reaction force on the specimen.

2. Method of claim 1 and including the step of load biasing the specimen during the second step, the duration of the second step being at least as long so that the reaction of the specimen to the bias has leveled off to a constant value.

3. Method as in claim 2 wherein the first and second step alternate in closed loop operation on the basis of detecting said leveling and commencing the next first step in dependence thereon.

4. Method as in claim 1 wherein the load phases include at least one of the following tension, compression, bending, torsion, shearing.

5. Method as in claim 4 wherein the first subjecting step is produced by a particular displacement of specific geometric value.

6. Method as in claim 1 wherein each of the first subjecting steps is the result of a particular displacement of constant amplitude, the reaction force exhibiting a particular relaxation during the particular displacement.

* * * * *